United States Patent [19]
Vari et al.

[11] Patent Number: 5,318,023
[45] Date of Patent: Jun. 7, 1994

[54] APPARATUS AND METHOD OF USE FOR A PHOTOSENSITIZER ENHANCED FLUORESCENCE BASED BIOPSY NEEDLE

[75] Inventors: Sandor G. Vari, Van Nuys, Calif.; Theodore Papazoglou, Athens, United Kingdom; Warren S. Grundfest, Los Angeles, Calif.

[73] Assignee: Cedars-Sinai Medical Center, Los Angeles, Calif.

[21] Appl. No.: 679,766

[22] Filed: Apr. 3, 1991

[51] Int. Cl.$^5$ .............................................. A61B 5/00
[52] U.S. Cl. ................................... 128/633; 128/634; 128/664; 128/665; 606/2; 606/13; 606/14; 606/15
[58] Field of Search ................. 606/2, 13–15; 128/633, 634, 664, 665

[56] References Cited

U.S. PATENT DOCUMENTS

| | | | |
|---|---|---|---|
| 4,140,109 | 2/1979 | Savic et al. | 606/21 |
| 4,273,127 | 6/1981 | Auth et al. | 606/16 |
| 4,556,057 | 12/1985 | Hiruma et al. | 606/14 |
| 4,887,600 | 12/1989 | Watson et al. | 606/15 |
| 4,930,516 | 6/1990 | Alfano et al. | |
| 5,042,494 | 8/1991 | Alfano . | |
| 5,074,306 | 12/1991 | Green et al. | 128/633 |
| 5,111,821 | 5/1992 | Potter . | |
| 5,131,398 | 7/1992 | Alfano et al. | |

*Primary Examiner*—Randall L. Green
*Assistant Examiner*—P. Zuttarelli
*Attorney, Agent, or Firm*—Lyon & Lyon

[57] ABSTRACT

A method and apparatus is disclosed for the instant intraoperative detection and biopsy of metastatic cancer using fluorescence spectroscopy. A photosensitizing agent selectively retained by cancerous tissue is administered prior to surgery. A fiberoptic probe integrated with a biopsy device illuminates the examined tissue and causes fluorescence which is recorded by a spectrograph and plotted as a spectral curve. The intensity ratio (S1/S2) for the fluorescence from the photosensitizing agent (S1) and autofluorescence (S2) for the examined tissue is compared with the intensity ratio at the same wavelengths for primary tumor and normal tissue. Tissue that displays an intensity ratio different from that of normal tissue can immediately be analyzed for the depth of tumor involvement and then excised for histological examination using the biopsy device.

12 Claims, 5 Drawing Sheets

APPARATUS AND METHOD OF USE FOR A PHOTOSENSITIZER ENHANCED FLUORESCENCE BASED BIOPSY NEEDLE

FIELD OF THE INVENTION

The present invention relates generally to a method and apparatus for the instant intraoperative detection and biopsy of metastatic cancer using fluorescence spectroscopy.

BACKGROUND

Perhaps no disease known to modern civilization is viewed with as much general fear as cancer. Heart attacks and strokes tend to be thought of as natural hazards of age, and either a normal end to a satisfactorily long life or, when they occur in middle-age, the wages of a sedentary lifestyle. In contrast, cancer is thought of as an unpredictable disease that strikes indiscriminately at rich and poor, fat and thin, old and young, as if it owed nothing to external causes. J. Cairns, *Mutation, Selection and Cancer*, Nature, Vol. 255, pp. 197-200 (1975).

Each year in the United States, approximately 600,000 new cases of cancer are diagnosed; and one out of every five people in this country will die from cancer, or from complications associated with its treatment. However, most of these cancer patients are not killed by their primary tumor. They succumb instead to metastasis: multiple, widespread tumor colonies established by malignant cells that detach themselves from the original tumor and travel through the body, often to distant sites. G. Nicholson, *Experimental Tumor Metastasis: Characteristics in Organ Specificity*, Bioscience, Vol. 28, No. 7, pp. 441-47 (July, 1978). If a primary tumor is detected early enough, it can usually be eliminated by surgery, radiation, chemotherapy or photodynamic therapy, or some combination of these treatments. Unfortunately, the metastatic colonies are harder to detect and eliminate because they often are not visible to the unaided eye, being microscopic in size or hidden within tissues or organs. This difficulty in detecting and eradicating metastasis enhances cancer's image as a fleeting and unpredictable disease.

Presently, primary tumor detection is accomplished by x-ray, ultrasonography, nuclear magnetic resonance (NMR), positron emission tomography (PET), chemical laboratory analysis and biopsy. However, metastatic dissemination from the primary tumor often is impossible to detect with these methods. As a result, there is a definite need for an accurate and sensitive technique to detect and sample these elusive metastatic colonies.

Every diagnosis of cancer must be documented by a definitive biopsy. In addition, biopsy is a crucial technique in the management of cancer. Since different types of neoplasms have their own responses to the various modalities of therapy, a histological diagnosis is imperative in planning the appropriate management of malignant disease. Moreover, biopsy provides the pathologist with adequate samples of tumor. In addition to the biopsy, an immediate frozen section during intraoperative procedures is often necessary for final diagnosis of malignancy. However, frozen section histology is both time consuming and expensive. Performed during the operation, this procedure requires the surgeon to halt the surgery midstream until the pathology of the suspected cancerous tissue is determined. Once determined, the operation can then be resumed. Consequently, the availability of a device that provides an instant indication of metastasis, as well as a simultaneous biopsy sample of the suspected tissue during the operative procedure would satisfy the need for a definitive biopsy and eliminate the disadvantages of frozen tissue histology.

With this in mind, it has been known for more than sixty years that some porphyrins are selectively retained by neoplastic tissue. A. Policard, *Etudes Sur Les Aspects Offerts Par De Tumeurs Experimentales Examineesa La Lumiere De Woods*, C. R. Seanc Soc. Biol. 91:1423-4 (1924). These same porphyrins also emit a characteristic dual-peaked red fluorescence after being exposed to light containing the appropriate wavelength to excite fluorescence. Although any fluorescent agent selectively retained by cancerous tissue can be used, Lipson in 1961, used these two properties of porphyrins to develop a primary tumor detection system. Lipson also introduced hematoporphyrin derivative (HPD) which demonstrated better tumor-localizing properties. R. L. Lipson, et al., *The Use of a Derivative of Hematoporphyrin in Tumor Detection*, J. Nat. Cancer Inst. 26:1-11 (1961). Dougherty then took advantage of HPD's photosensitizing properties to eradicate tumors, opening the door to HPD's use as a therapeutic cancer modality. Since that time, HPD's primary importance in the cancer arena has been as a potential cancer treatment, and extensive investigation has been done to refine its use. T. Dougherty, *C.R.C. Critical Review in Oncology/Hematology*, S. David, E. D. (C.R.C. Press, Florida, 1984).

Termed, "Hematoporphyrin Derivative Photodynamic Therapy," HPD's mechanism in cancer therapy is based on its affinity for malignant tumors relative to other tissues. When injected intravenously, HPD localizes at higher levels in malignant tumor tissues than in normal tissues. The HPD is then activated by light to catalyze the production of singlet oxygen from available triplet oxygen. Although the exact mechanism of necrosis is unclear, it has been suggested that the reactive singlet oxygen oxidizes unsaturated carbon-carbon bonds in amino acids and fatty acids. The ensuing loss of the structural integrity of cellular macromolecules results in cytocidal effects and tumor necrosis. Li, et al., *Application of HPD and Laser-Induced Photo Dynamical Reaction in the Treatment of Lung Cancer*, Laser in Surgery and Medicine, 4:31-7 (1984).

This use of HPD in photodynamic cancer treatment is a very exiting and rapidly developing possibility. However, a complete cure for cancer is impossible without specific detection and ablation of those cancer cells that have disseminated throughout the organism via the lymphatic or circulatory system. The present invention deals with this problem of metastasis and facilitates a potential cancer cure by utilizing HPD's tumor-seeking properties and fluorescence to instantly detect and simultaneously biopsy cancerous tissue undetected by conventional methods.

Although much of the research involving HPD has been with regard to cancer treatment, several investigators have looked at HPD's tumor detection capabilities. However, the goal of this detection work has been to use surface fluorescence to localize carcinoma in situ which by definition has not penetrated the basement membrane, and thus is not metastasizing. In contrast, the present invention is capable of detecting and biopsying metastatic sites, as well as determining tumor depth and size. In fact, the present invention is based in part on the discovery that metastatic sites which generally are undetected by conventional diagnostic methods produce a fluorescence spectra different from that of primary tumor and normal tissue. The photosensitizer enhanced fluorescence spectra of metastatic sites are consistently and significantly higher than the fluorescence spectra of both the primary tumor and normal tissue.

Profio, et al. described a fluorescence bronchoscopy system for localizing small lung tumors and carcinomas in situ by HPD fluorescence. E. Profio, *Fluorescence Bronchoscopy for Localization of Carcinoma In Situ*, Med. Phys. 10 (1), pp. 35-39 (Jan./Feb. 1983). Ankerst, Montan and Svanberg each studied HPD laser-induced fluorescence in normal and tumor rat tissue to determine optimal HPD surface fluorescence for tumor detection. J. Ankerst, et al., *Laser-Induced Fluorescence Studies of Hematoporphyrin Derivative (HPD) in Normal and Tumor Tissue of Rat*, Applied Spectroscopy, Vol. 38, No. 6, pp. 890-96 (1984); S. Montan, *Multicolor Imaging and Contrast Enhancement in Cancer-Tumor Localization Using Laser-Induced Fluorescence in Hematoporphyrin-Derivative-Bearing Tissue*, Optics Letters, Vol. 10, No. 2, pp. 56-8 (February, 1985); and K. Svanberg, *Fluorescence Studies of Hematoporphyrin Derivative in Normal and Malignant Rat Tissue*, Cancer Research, 46:3806-808 (August, 1986). Kato, et al. described four different bronchoscopic fluorescence detection systems that have facilitated the localization of HPD-labelled squamous cell carcinoma of the trachea and the central bronchi. H. Kato, et al., *Early Detection of Lung Cancer by Means of Hematoporphyrin Derivative Fluorescence and Laser Photoradiation*, Clinics in Chest Medicine, Vol. 6, No. 2, pp. 337-53 (June, 1985).

Others have attempted to utilize HPD's tumor seeking properties to detect cancer, but have failed. This failure was apparently due to an intrinsic abundance of free porphyrins in cancerous tissue and HPD's uptake in normal tissue. It therefore was concluded that HPD did not provide a good in vivo technique for detection. The present invention, however, overcomes these failures, and is capable of detecting cancer in situ as well as difficult to find metastasis. Moreover, once detected, the present invention also allows for the immediate biopsy of metastatic sites.

In U.S. Pat. No. 4,930,516 to R. R. Alfano, there is described a method and apparatus for detecting the presence of tumors in situ using the native visible luminescence of the cell. The invention is based exclusively on the intrinsic fluorescence of the cell produced by native flavins and porphyrins found in abundance in subcellular organelles.

SUMMARY OF THE INVENTION

The present invention for the instant intraoperative detection and biopsy of metastatic cancer involves, according to one embodiment of the invention, administering prior to surgery, a photosensitizing agent selectively retained by cancerous tissue. The region to be examined is then illuminated with a beam of monochromatic light and/or incoherent light filtered to a specific wavelength from the fiber optic portion of the fiber optic biopsy probe, and the emitted fluorescence is recorded by a spectrograph and plotted as a spectral curve. The intensity ratio (S1/S2) of the photosensitizer induced fluorescence (S1) and autofluorescence (S2) for the examined tissue is compared with the intensity ratio at the same wavelengths for primary tumor and normal tissue. All tissue that displays a fluorescence pattern different from normal can immediately be examined for tumor depth, excised using the biopsy portion of the fiber optic biopsy probe and then subjected to histological examination.

The apparatus for the present invention, according to one embodiment, includes a light source, a spectrograph, a video camera, a digitizer, a computer, a display means for measuring and comparing the intensity of the emitted light over a plurality of wavelengths, and a biopsy device.

The apparatus of the present invention according to another embodiment, includes a light source, optical filters, a photo detector, a display means for measuring the emitted light at different wavelengths and a biopsy device. It is to be understood however, that other embodiments may be utilized and that structural changes may be made without departing from the scope of the invention. The following detailed description is therefore, not to be taken in a limiting sense, and the scope of the present invention is best defined by the appended claims.

It is a general object of the present invention to provide an apparatus and method for the instant intraoperative detection of metastasis not visible to the naked eye.

It is another object of the present invention to provide an apparatus and method for the instant intraoperative detection of metastasis undetected by conventional diagnostic methods employed to detect primary tumors.

It is still another object of the present invention to provide an apparatus and method for the instant intraoperative detection of metastasis using fluorescence spectroscopy.

It is a further object of the present invention to provide an apparatus and method for the instant determination of the extent of metastatic involvement in an affected tissue.

It is still further an object of the present invention to provide an apparatus and method for immediately excising upon detection the suspected metastatic tissue.

It is also an object of the present invention to eliminate the time and expense incurred by frozen section histology.

These and other objects will become readily apparent to those skilled in the art from the following description and the appended claims.

BRIEF DESCRIPTION OF THE DRAWINGS

FIG. 1 is a schematic diagram of an experimental optical biopsy

DETAILED DESCRIPTION OF THE INVENTION

The present invention is directed to a method and apparatus for the instant intraoperative detection and biopsy of metastatic cancer using fluorescence spectroscopy.

The experimental arrangement used to measure the fluorescence spectra during abdominal exploration included a Helium-cadmium laser operating at 442 nm as an excitation source. A hand held 400 micron core diameter fiber was directed at the tissue producing a low power (17 mw) illumination. Using the same fiber, reflected and emitted light was returned to the input of a SPEX 500 spectrometer. The spectrometer output was directed to a Silicon Diode Array (Model A 1420 B, EG&G) coupled into an optical multi-channel analyzer (OMA III EG&G). Signals from the OMA were then displayed on a screen for immediate examination. A series of normal spectra were recorded from the left medial thigh muscles for baseline. The fluorescence intensities at 540 nm (auto- fluorescence) and 630 nm (Photofrin II) were simultaneously monitored. By using the ratio of these intensities ($I_{630\ nm}/I_{540\ nm}$), a relative value could be assigned to each area studied. An increased value of the ratio of intensities ($I_{630\ nm}/I_{540\ nm}$) signaled a possible metastatic site. Tissues displaying such an increased ratio of intensities were removed using a biopsy device integrated with the fiberoptic probe and subjected to histological examination.

In detecting the presence of cancerous tissue in accordance with the invention, the ratios of two probe signals S1 and S2 (S1/S2) are first determined for a known non-cancerous region. S1 represents the fluorescence intensity at 630 nm (Photofrin II); and S2 represents the fluorescence intensity at 540 nm (auto-fluorescence). An increased value of the S1/S2 ratio signals a possible metastatic site.

Figure 1A:
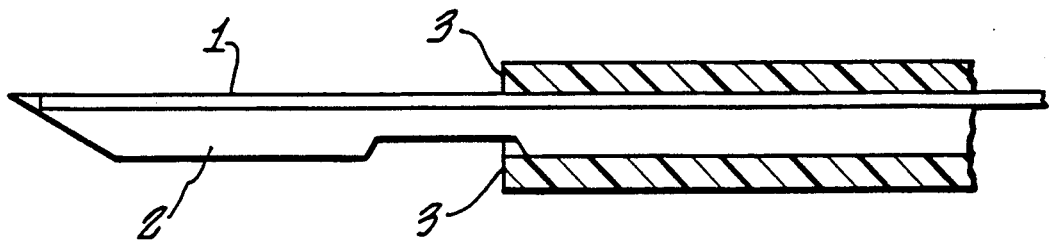
FIG. 1A is a cross section of the end portion of the experimental optical biopsy probe.
Figure 1B:
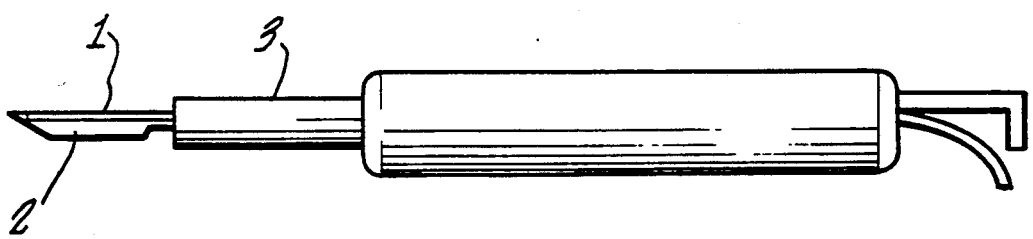
FIG. 1B is a schematic diagram of the experimental biopsy probe.

Alternatively, the light source may comprise any device emitting substantially monochromatic light and/or incoherent light filtered to a specific wavelength. The fiber optic probe is composed of either multiple or single fiber arrays, the core diameter of which is preferably about 400 microns. Integrated with the fiber optic probe is a biopsy needle (Baxter, Tri-Cute or any conventional biopsy needle) for instant determination of tumor depth and immediate tissue removal. The biopsy needle can be calibrated (inches, millimeters) to visually determine the depth of tumor involvement in the affected tissue. A schematic diagram of an experimental optical biopsy probe is illustrated in FIG. 1. The optical probe 1 can be integrated in any manner to the top surface of the biopsy blade 2, and then housed in a probe casing 3. However, it is understood that other embodiments may be utilized and structural changes made to the optical biopsy probe without departing from the scope of the invention.

The fluorescence emitted from cancerous and normal tissues of twenty male Lobund-Wistar rats was investigated. All tumors were subcutaneously implanted by inoculating $10^5$ Viable cells of Pollard rat prostatic adenocarcinoma (PA-III) into the right flank of each animal. This tumor model was selected because it is known to metastasize uniformly and spontaneously from extravascular sites only through ipsilateral lymphatic channels. Because of this tumor's unique, predictable spread, the contralateral side of the animal could be used as a control. In addition, cancer detection is facilitated with this model because rats with PA-III cells survive beyond forty days after implantation without evidence of physical impairment.

After forty-two days of observation, Photofrin II (QLT Phototherapeutics, Inc., Vancouver, Canada) was administered intraperitoneally twenty four - forty eight hours prior to surgical exploration in doses ranging from 0.75-7.5 mg/kg. Eighteen animals were divided into eight groups and injected with four different concentrations of Photofrin II (7.5 mg/kg, 2.5 mg/kg, 1.5 mg/kg and 0.75 mg/kg). Metastatic detection was performed during abdominal exploration of the renal, para-aortic, and iliac lymph nodes after laparotomy. The rats were anesthetized with ketamine 40 mg/kg and Xylazine 5.0 mg/kg intraperitoneally, and the abdomens opened through a midline incision. Advancing caudally to cranially, ipsilateral inguinal, iliac, para-aortal and renal lymph nodes were scanned. The areas were scanned in a contact mode with a hand held fiber along the iliac artery to medial and along the aorta to the para-aortic and renal lymph nodes (50 acquisition points/second, 3–4 detection sites/minute, going back and forth. Otherwise, the number of sites could increase.)

Nineteen abnormal tissue samples were removed for histological analysis, eleven of which were larger than 5 mm. Laser-induced fluorescence spectroscopy revealed malignancy in all eleven cases. In eight excised tissue samples with dimensions less than 5 mm, laser-induced fluorescence spectroscopy suggested malignancy, but histology confirmed malignancy in only three samples (see Table I below). Lymph nodes and tissues where tumor was detected were immediately excised for further histologic examination. The contralateral side was scanned in the same manner and contralateral lymph nodes were excised for histological examination. Fluorescence spectra were also obtained from the liver, kidney, stomach, skin, muscle and large and small bowel.

TABLE I

| Tissue Samples Identified As Malignant By LIFS (n = 19) | | |
|---|---|---|
| | Histological Identification | |
| Tumor Size | Malignant | Normal |
| >5 mm | 11 | 0 |
| <5 mm | 3 | 5 |
| p < .01 (Fisher's exact test) | | |

Figure 2:
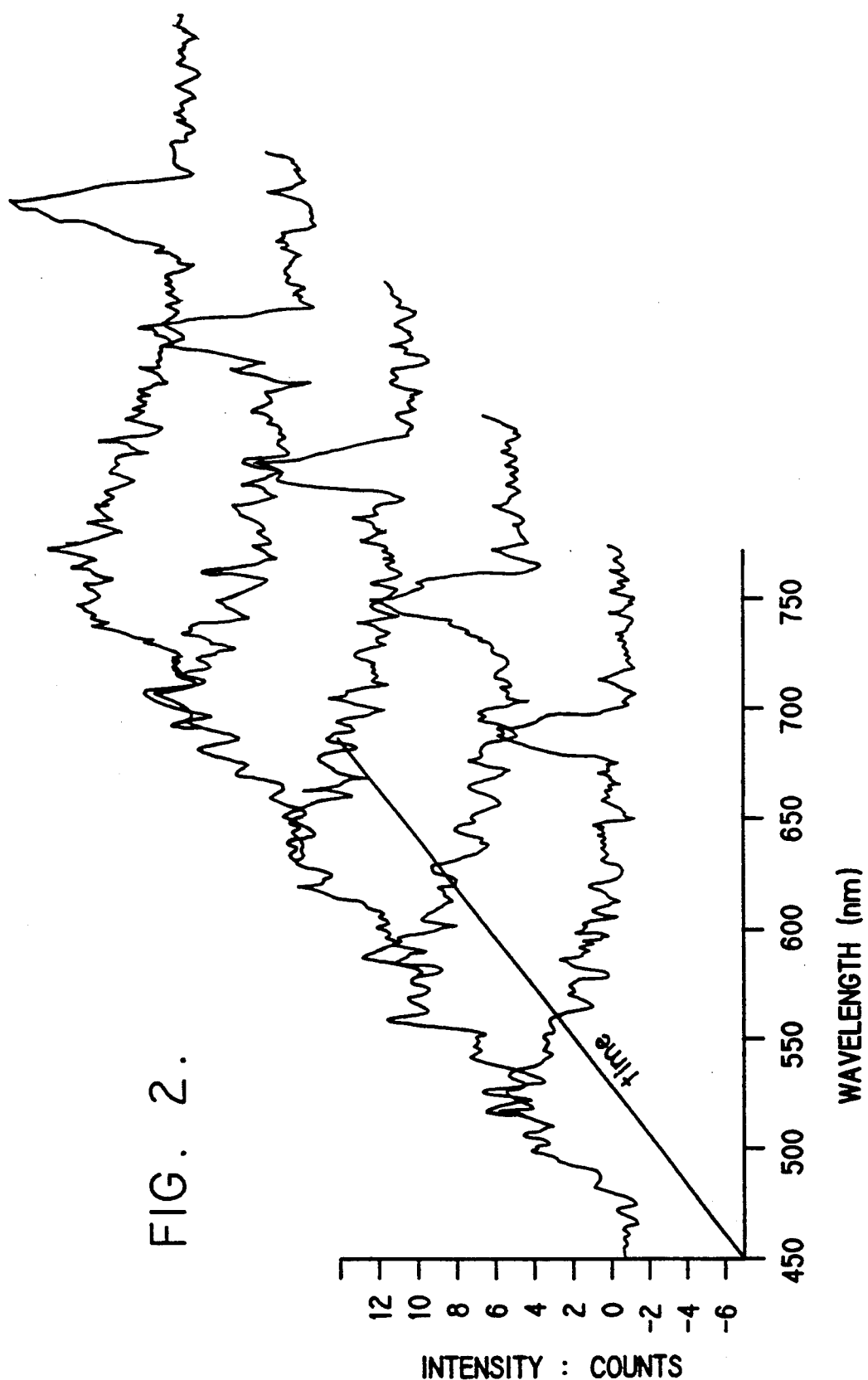
FIG. 2 is a fluorescence spectra of rat malignant tissue containing Photofrin II and the autofluorescence spectra of rat tissue over time.

FIG. 2 illustrates the time-related spectral curves for cancerous and normal rat tissue after Photofrin II administration. The Y-axis represents fluorescence intensity, the X-axis represents wavelength and the Z-axis represents time. The fluorescence spectrum was recorded at every 20th millisecond using a OMA III system while puncturing the targeted rat tissue with the optical biopsy needle. Both the autofluorescence of the tissue and the fluorescence signal of the malignant tissue containing Photofrin II were recorded. The autofluorescence peak is located at 540 nm, and a more prominent peak representing metastasis is located at 630 nm. Note that the intensity of the prominent peak at 630 nm increases as the optical biopsy needle is advanced into the metastasis.

Figure 3:
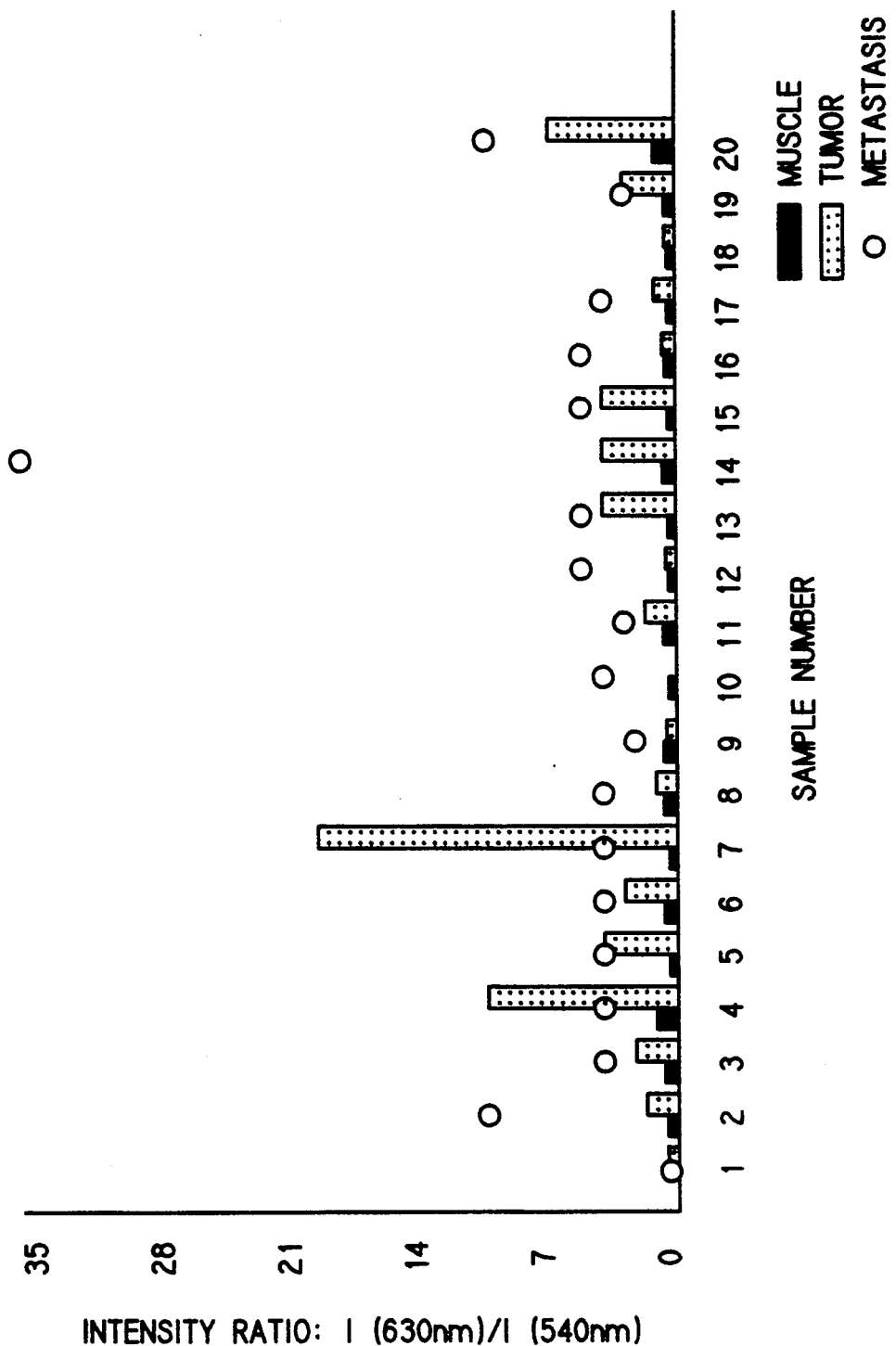
FIG. 3 is a graphic distribution of the fluorescence intensity ratio of Photofrin II to autofluorescence for various Photofrin II doses in different rat tissues.

FIG. 3 illustrates the intensity ratio of Photofrin II to autofluorescence for the Photofrin II distribution in rat muscle, primary tumor (right flank) and abdominal metastasis. The Y-axis represents the Intensity Ratio ($I_{630 nm}/I_{540 nm}$), the X-axis represents the particular sample number tested, and the bars represent the three different areas scanned: the circle illustrating metastasis, the shaded bar illustrating tumor, and the solid bar illustrating normal muscle mass. The intensity ratio of Photofrin II fluorescence at 630 nm and tissue autofluorescence at 540 nm was calculated for each of 20 rats to eliminate interference from background fluorescence due to intrinsic porphyrins in cancerous tissue and limited porphyrin uptake in normal tissue. Rats No. 1 and No. 18 were used as controls. The intensity ratio was calculated from fluorescence produced by four different doses of Photofrin II (0.75 mg/kg, 1.5 mg/kg, 2.5 mg/kg and 7.5 mg/kg) and two postinjection times of 24 and 48 hours. The prominent peaks for metastasis demonstrates a consistent and significantly higher uptake of Photofrin II by metastasis than by primary tumor for all post injection times.

Figure 4:
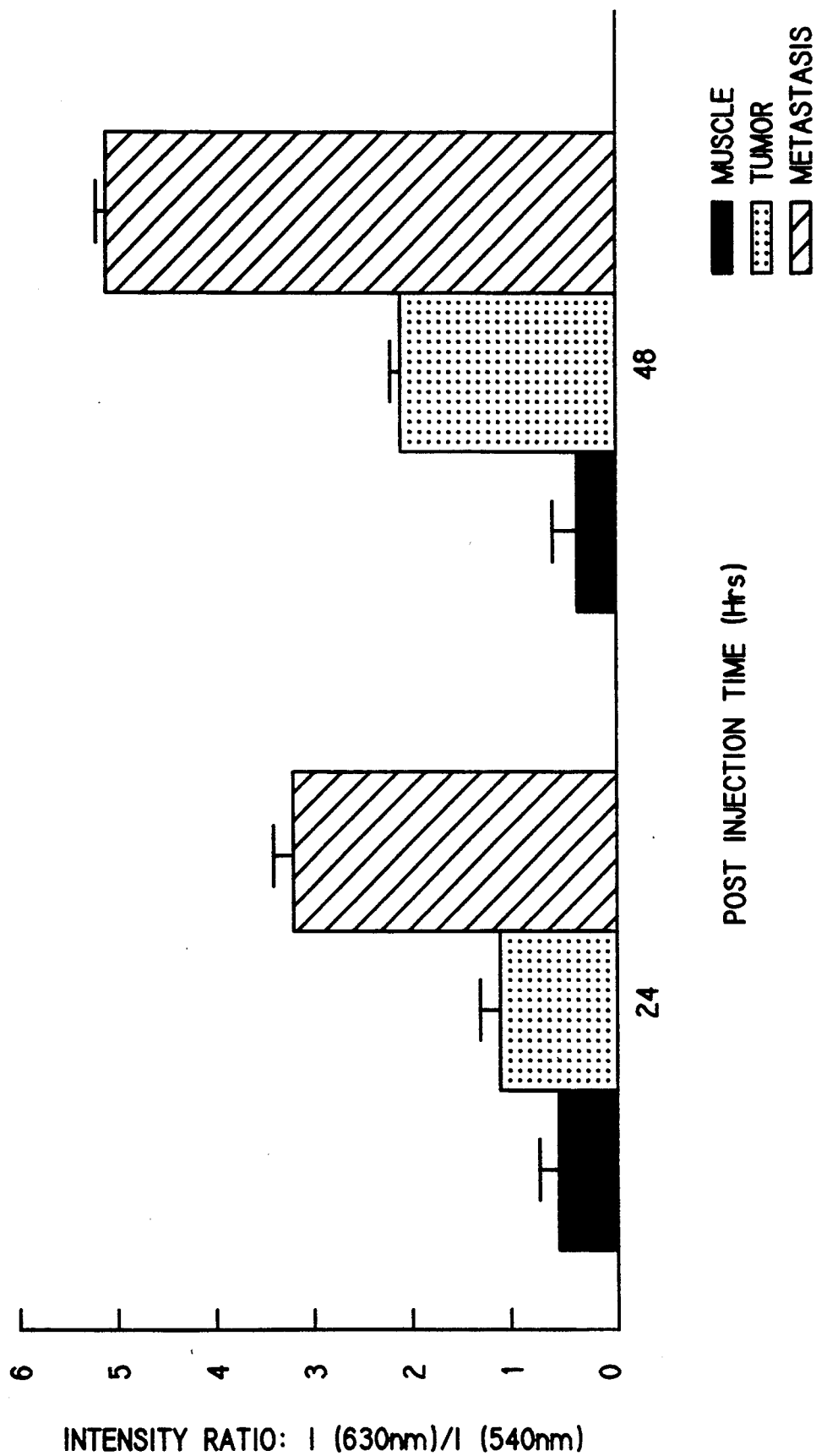
FIG. 4 is a graphic distribution of the fluorescence intensity ratio of Photofrin II to autofluorescence for the accumulation of Photofrin II in specific rat tissues over time.

The graph in FIG. 4 uses the same intensity ratio of Photofrin II fluorescence to autofluorescence to demonstrate the optimum time for Photofrin II accumulation in muscle, primary tumor, and metastasis after injection. Here again, the Y-axis represents the Intensity Ratio, but the X-axis represents the two post-injection times of 24 hours for the 3 bars left of center, and 48 hours for the three bars right of center. The three bars represent the three different areas of the body where the intensity ratio was monitored: the diagonal shading representing metastasis, the dotted shading representing tumor and the solid bar representing normal muscle mass. Signals at the site of the primary tumor and lymph nodes with metastasis show a higher ratio at 48 hours than at 24 hours after Photofrin II administration. In contrast, the ratio at the thigh muscle site was higher at 24 hours than at 48 hours. (See also Tables II and III below).

TABLE II

| Intensity Ratio: $I_{630nm}/I_{540nm}$ vs. Time After Administration of Photofrin II Injection dose: 1.5 mg/kg | |
|---|---|
| Tissue | Intensity Ratio ($I_{630nm}/I_{540nm}$) |
| Time after administration: 24 hrs; n = 2 | |
| Muscle | 0.5 ± 0.1 |
| Tumor | 1.0 ± 0.1 |
| Metastases | 3.3 ± 0.1 |
| Time after administration: 48 hrs; n = 2 | |
| Muscle | 0.22 ± 0.15 |
| Tumor | 2.55 ± 1.5 |
| Metastases | 5.00 ± 0.1 |

TABLE III

| Intensity ratio: $I_{630nm}/I_{540nm}$ vs. Photofrim II Administration Dose Time After Administration: 48 Hours | | |
|---|---|---|
| Tissue | Photofrin II Dose (mg/kg) | |
| | 0.75 (n = 3) | 1.5 (n = 2) |
| Muscle | 0.34 ± 0.06 | 0.22 ± 0.15 |
| Tumor | 0.80 ± 0.7 | 2.55 ± 1.5 |
| Metastases | 2.5 ± 0.8 | 5.00 ± 0.1 |
| | 2.5 (n = 2) | 7.5 (n = 2) |
| Muscle | 0.36 ± 0.36 | 0.48 ± 0.24 |
| Tumor | 1.82 ± 1.9 | 3.64 ± 3.65 |
| Metastases | 5.2 ± 3.36 | 4.64 ± 2.99 |

Figure 5:
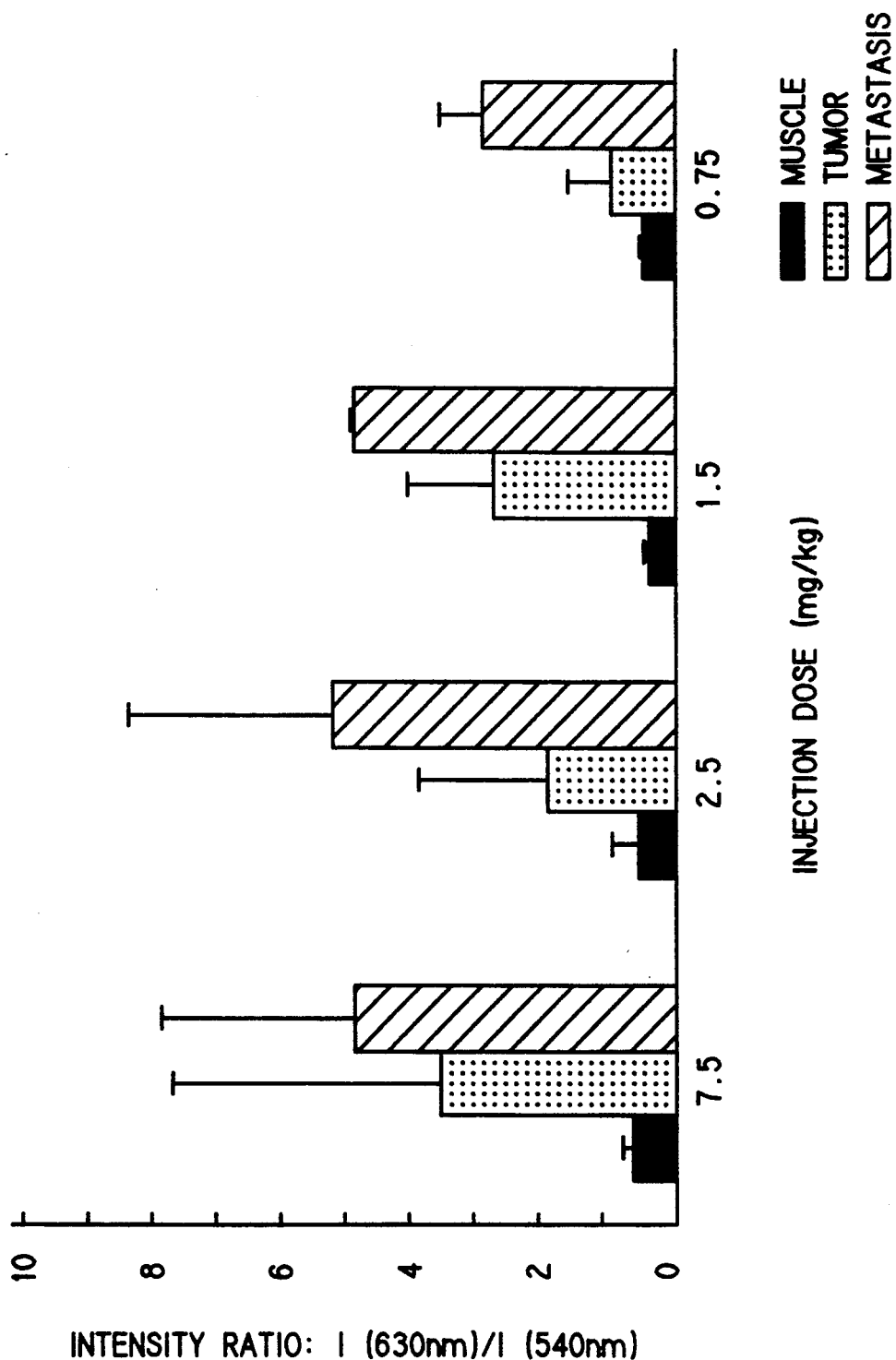
FIG. 5 is a graphic distribution of the fluorescence intensity ratio of Photofrin II to autofluorescence for different doses of Photofrin II in specific rat tissues forty-eight hours after administration.

FIG. 5 demonstrates the optimum Photofrin II dosage range for metastasis detection using the same fluorescence intensity ratio of Photofrin II fluorescence to autofluorescence for different doses 48 hours after administration. The Y-axis represents the Intensity Ratio while the X-axis represents the four different Photofrin II injection doses tested. The first three bars from the left side of the graph illustrate the Intensity Ratio at a dose of 7.5 mg/kg, the second three bars from the left illustrate the Intensity Ratio at a dose of 2.5 mg/kg, the third three bars illustrate the Intensity Ratio at a dose of 1.5 mg/kg, while the last three bars illustrate the Intensity Ratio at a dose of 0.75 mg/kg. Again, the bars with diagonal shading represent metastasis, the bars with dotted shading represent tumor and the solid bars represent normal muscle tissue. The bar graph illustrates no significant difference in the metastasis intensity ratio for Photofrin II doses of 1.25 mg/kg, 2.5 mg/kg and 7.5 mg/kg. Although the metastasis intensity ratio at 0.75 mg/kg was somewhat lower than at the other three dosages, it was still useful to distinguish metastatic tissue from primary tumor.

In summary, it has been discovered that when the ratio of intensity of Photofrin II fluorescence to autofluorescence is observed ($I_{630 nm}/I_{540 nm}$), there is a consistent and significant difference between metastasis and primary tumor as well as metastasis and normal or benign tissue. The ratio readings for metastasis are consistently higher, by a significant margin, than for primary tumor and normal tissue. Based on this knowledge, the detection and subsequent biopsy of disseminated metastatic cancer can be made for cancer diagnosis and treatment.

We claim:

1. A method for the detection and biopsy of metastatic cancer comprising:
   a. administering intravenously an effective amount of a photosensitizing agent selectively retained by cancerous tissue and capable of lightinduced fluorescence,
   b. exciting a tissue to be examined with a beam of light from a light source,
   c. examining the tissue of step (b) by contacting it with the beam of light from the light source of step (b) to induce fluorescence,
   d. observing the fluorescence emitted from the examined tissue of step (c) and a tissue whose condition is known to be without cancer, each observation made at two difference wavelengths in order to calculate a first fluorescence intensity ratio for the examined tissue and a second fluorescence intensity ratio for the tissue whose condition is known to be without cancer,
   e. determining if the tissue is cancerous by observing whether the first fluorescence intensity ratio is different than the second fluorescence intensity ratio,
   f. excising for histological examination the cancerous tissue using a hollow biopsy needle integrated with the light source.

2. A method for the detection and biopsy of metastatic cancer comprising:
   a. administering intravenously an effective amount of a photosensitizing agent selectively retained by cancerous tissue and capable of light-induced fluorescence,
   b. exciting a tissue to be examined with a beam of light from a light source,
   c. examining the tissue of step (b) by contacting it with the beam of light from the light source of step (b) to induce fluorescence, d. observing the fluorescence emitted from the examined tissue of step (c) and a tissue whose condition is known to be without cancer, each observation made at two different wavelengths in order to calculate a first fluorescence intensity ratio for the examined tissue and a second fluorescence intensity ratio for the tissue whose condition is known to be without cancer, e. determining if the tissue is cancerous by observing whether the first fluorescence intensity ratio is different than the second fluorescence intensity ratio, f. determining the depth of cancer involvement in the cancerous tissue using a biopsy blade integrated with the light source, and g. excising for histological examination the cancerous tissue using a hollow biopsy needle.

3. A method for the detection and biopsy of metastatic cancer comprising:

a. administering intravenously an effective amount of a photosensitizing agent selectively retained by cancerous tissue and capable of light-induced fluorescence, b. exciting a tissue to be examined with a beam of light that is at least substantially monochromatic or incoherent light filtered to a specific wavelength, c. examining the tissue of step (b) by contacting it with the beam of light from the light source of step (b) to induce fluorescence, d. observing the fluorescence emitted from the examined tissue of step (c) and a tissue whose condition is known to be without cancer, each observation made at two different wavelengths in order to calculate a first fluorescence intensity ratio for the examined tissue and a second fluorescence intensity ratio for the tissue whose condition is known to be without cancer.

e. determining if the tissue is cancerous by observing whether the first fluorescence intensity ratio is different than the second fluorescence intensity ratio, f. excising for histological examination the cancerous tissue using a hollow biopsy needle integrated with the light source.

4. A method for the detection and biopsy of metastatic cancer comprising:

a. adminsistering intravenously an effective amount of a photosensitizing agent selectively retained by cancerous tissue and capable of light-induced fluorescence, b. exciting a tissue to be examined with a beam of light that is at least substantially monochromatic or incoherent light filtered to a specific wavelength, c. examining the tissue of step (b) by contacting it with the beam of light from the light source of step (b) to induce fluorescence, d. observing the fluorescence emitted from the examined tissue of step (c) and a tissue whose condition is known to be without cancer, each observation made at two different wavelengths in order to calculate a first fluorescence intensity ratio for the examined tissue and a second fluorescence intensity ratio for the tissue whose condition is known to be without cancer.

e. determining if the tissue is cancerous by observing whether the first fluorescence intensity ratio is different than the second fluorescence intensity ratio, f. determining the depth of cancer involvement in the cancerous tissue using a hollow biopsy needle integrated with the light source, and g. excising for histological examination the cancerous tissue using the biopsy needle.

5. The method of claim 4 and wherein determining if cancerous tissue is present includes producing a signal corresponding to the ratio between the intensities at two different wavelengths and then displaying the signal.

6. A method for the detection and biopsy of metastatic cancer comprising:

a. administering intravenously an effective amount of a photosensitizing agent selectively retained by cancerous tissue and capable of light-induced fluorescence, b. exciting a tissue to be examined with a beam of monochromatic light or incoherent light filtered to a specific wavelength from a light source, c. examining the tissue of step (b) by contacting it with the beam of light from the light source of step (b) to induce fluorescence, d. generating a fluorescence spectrum of light emitted by the examined tissue, e. determining the ratio of intensities at two different wavelengths for the examined tissue and then comparing the ratio of intensities at the same wavelengths for primary tumor and normal tissue, f. determining that the tissue is cancerous if the intensity ratio for examined tissue is different than the ratio of intensity at the same wavelengths for normal tissue, g. determining the depth of cancer involvement in the cancerous tissue using a hollow biopsy needle integrated with the light source, and h. excising for histological examination tissue that displays a fluorescence pattern different from that of normal tissue using the biopsy needle.

7. The method of claim 6 and wherein the two different wavelengths from which fluorescence is observed are 630 nm and 540 nm.

8. The method of claim 6 and wherein determining the depth of cancer involvement of the affected tissue comprises using a calibrated biopsy needle.

9. The method of claim 2 wherein the cancerous tissue is diagnosed and excised with an apparatus comprising:

a. a light source capable of inducing fluorescence of photosensitizing agents which agents are selectively retained by cancerous tissue following injection, and b. a hollow biopsy needle to remove suspected cancerous tissue, the biopsy needle having thereon the light source.

10. The method of claim 2 wherein the cancerous tissue is diagnosed and excised with an apparatus comprising:

a. a light source capable of emitting substantially monochromatic light or incoherent light filtered to a specific wavelength to induce fluorescence of photosensitizing agents, which agents are selectively retained by cancerous tissue following injection, and b. a hollow biopsy needle to remove suspected cancerous tissue, the biopsy needle having thereon the light source.

11. The method of claim 10 and wherein the light source comprises multiple or single fiber arrays with a core diameter from about 400 microns.

12. The method claim 10 and wherein the needle is calibrated to measure the depth of cancer involvement in the cancerous tissue.

* * * * *